Figure 1:
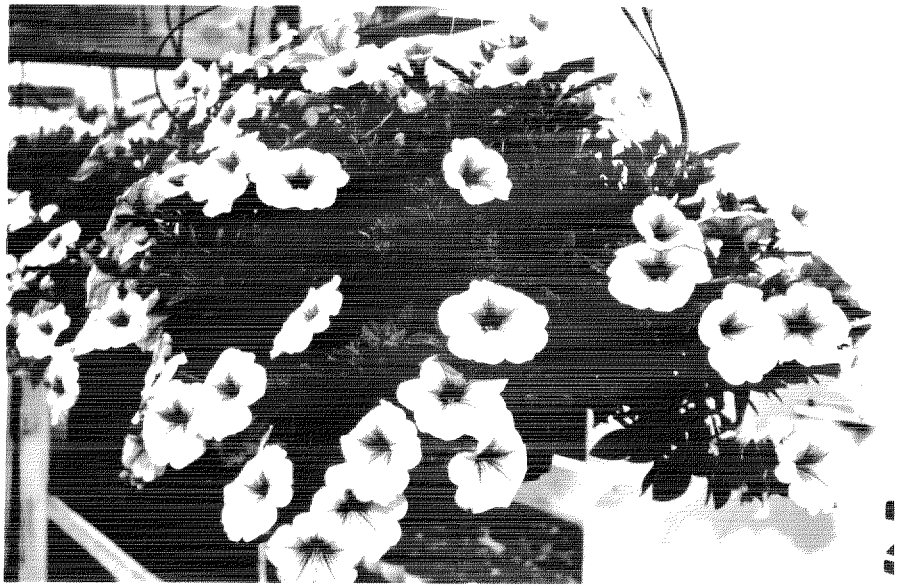

US00PP10045P

United States Patent [19]

Rother

[11] Patent Number: Plant 10,045

[45] Date of Patent: Sep. 30, 1997

[54] PETUNIA PLANT NAMED SUNVALE

[76] Inventor: Reinhard W. Rother, 56 Emerald Monbulk Road, Emerald, Victoria 3782, Australia

[21] Appl. No.: 680,164

[22] Filed: Jul. 15, 1996

[51] Int. Cl.[6] ..... A10H 5/00

[52] U.S. Cl. ..... Plt./68.1

[58] Field of Search ..... Plt./68.1

*Primary Examiner*—James R. Feyrer
*Attorney, Agent, or Firm*—R. A. Whealy

[57] ABSTRACT

A distinct cultivar of Petunia plant named 'Sunvale', characterized by its large light purple flowers that face upwards; compact growth habit and moderate growth rate; somewhat upright, but spreading plant habit; freely branching habit; early flowering; very floriferous with numerous flowers per plant; and tolerance to rain, drought and temperature extremes.

2 Drawing Sheets

The present invention relates to a new and distinct cultivar of Petunia plant, botanically known as *Petunia axillaris*, and hereinafter referred to by the cultivar name 'Sunvale'.

The new cultivar is a product of a planned breeding program conducted by the inventor in Emerald, Victoria, Australia. The objective of the breeding program was to create new Petunia cultivars having large flowers, a spreading plant habit, and desirable flower colors.

The new cultivar originated from a cross made by the inventor of the Petunia cultivar 'Sumi 932'(not patented) as the male or pollen parent with the Petunia cultivar 'Pink Victory' (not patented) as the female or seed parent.

The cultivar 'Sunvale' was discovered and selected by the inventor as a flowering plant within the progeny of the stated cross in a controlled environment in Emerald, Victoria, Australia. Asexual reproduction of the new cultivar by terminal cuttings taken at Emerald, Victoria, Australia, has shown that the unique features of this new Petunia are stable and reproduced true to type in successive generations.

The cultivar 'Sunvale' has not been observed under all possible environmental conditions. The phenotype may vary somewhat with variations in environment such as temperature and light intensity, without, however, any variance in genotype. The following observations, measurements and comparisons describe plants grown in Emerald, Victoria, Australia, under commercial production conditions.

The following traits have been repeatedly observed and are determined to be the unique characteristics of 'Sunvale'. These characteristics in combination distinguish 'Sunvale' as a new and distinct cultivar:

1. Large light purple flowers that face upwards.
2. Compact growth habit and moderate growth rate.
3. Somewhat upright, but spreading plant habit.
4. Freely branching habit. Plants do not require pinching.
5. Early flowering.
6. Very floriferous with numerous flowers per plant.
7. Tolerant to rain, drought and temperature extremes.

The cultivar 'Sunvale' is similar in flower color to the parent cultivar 'Pink Victory'. The cultivar Sunvale differs from the cultivar 'Pink Victory' in the following characteristics:

1. Plants of the cultivar 'Sunvale' are more upright and less spreading than plants of the cultivar 'Pink Victory'.
2. Leaves of the cultivar 'Sunvale' are elliptic in shape whereas leaves of the cultivar 'Pink Victory' are ovate in shape.
3. Leaves of the cultivar 'Sunvale' are smaller than leaves of the cultivar 'Pink Victory'.
4. Leaves of the cultivar 'Sunvale' are more pubescent than leaves of the cultivar 'Pink Victory'.
5. Internode length on plants of the cultivar 'Sunvale' is shorter than plants of the cultivar 'Pink Victory'.

6. New shoots of the cultivar 'Sunvale' have anthocyanin whereas new shoots of the cultivar 'Pink Victory' are green and apparently do not have anthocyanin.
7. Plants of the cultivar 'Sunvale' have broader corolla diameter but narrower flower tube diameter compared to plants of the cultivar 'Pink Victory'.
8. Plants of the cultivar 'Sunvale' have narrower sepals and sepals are elliptic than plants of the cultivar 'Pink Victory' that has spatulate sepals.
9. Pedicels of the cultivar 'Sunvale' are longer than pedicels of the cultivar 'Pink Victory'.
10. The flower throat and tube color of plants of the cultivar 'Sunvale' are light purple whereas the flower throat and tube color of plants of the cultivar 'Pink Victory' are light violet.
11. The petal color of plants of the cultivar 'Sunvale' are darker than the petal color of plants of the cultivar 'Pink Victory' .
12. The stigma is above the anthers on plants of the cultivar 'Sunvale' whereas the stigma is below the anthers on plants of the cultivar 'Pink Victory'.
13. The anther color of plants of the cultivar 'Sunvale' is violet whereas the anther color of plants of the cultivar 'Pink Victory' is blue. A detailed comparison of the cultivars 'Sunvale' and 'Pink Victory' appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical hanging basket plant of the 0cultivar Sunvale.

The second photograph comprises a close-up view of individual flowers of the cultivar Sunvale.

Flower and foliage colors may appear different than the actual colors due to light reflectance.

In the following description, color references are made to The Royal Horticultural Society Colour Chart except where general terms of ordinary dictionary significance are used. Measurements are averages from ten specimens selected at random from five plants.

Botanical classification: *Petunia axillaris* cultivar 'Sunvale'.

Parentage:

*Male or pollen parent.*—*Petunia axillaris* cultivar 'Sumi' 932 (not patented).

*Female or seed parent.*—*Petunia axillaris* cultivar 'Pink Victory' (not patented).

Propagation:

*Type cutting.*—Terminal vegetative cuttings.

*Time to initiate roots.*—About ten days at 21C soil temperature.

*Rooting habit.*—Numerous, fine, fibrous, and well-branched.

Plant description:

*Form.*—Indeterminate, decumbent, diffuse spreading, viscid, glandular pubescent.

*Branching habit.*—Freely branching.

*Plant height.*—About 19.4 cm.

*Plant width.*—About 52.6 cm.

*Vigor.*—Moderate.

*Crop time.*—About nine weeks from a unrooted cutting to a 10.5-cm finished and flowering container.

*Foliage description.*—Leaves simple, generally symmetrical, sessile, and long persisting. Leaves at first whorled, later alternate, somewhat fleshy. Size (largest leaves): Length: About 5.2 cm. Width: About 3.2 cm. Thickness: About 1 mm. Shape: Elliptic. Aspect: Horizontal to slanting upwards. Apex: Acute. Base: Attenuate. Margin: Entire. Texture: Moderately pubescent. Color: Young foliage upper side: 137A. Young foliage under side: 147B. Mature foliage upper side: 137A. Mature foliage under side: 147B.

*Stem description.*—Stems upright to spreading, hirsute. Stem diameter: About 3 mm. Internode length: Medium, about 2.7 cm. Stem color: Green, 144A.

Flower description:

*Flower type and habit.*—Large, single, salverform flowers, facing upwards, axillary. Calyx five-parted, petals united into a flower tube.

*Natural flowering season.*—Long day responsive, continuously flowers from spring through fall in Northern Hemisphere.

*Quantity.*—Numerous flowers per plant.

*Corolla.*—Diameter: About 7.1 cm. Height: About 5.5 cm. Flower tube width at distal end: About 1.1 cm. Petal quantity: Five, fused. Petal apex: Medium. Margin: Entire, undulating Texture: Pubescent on outside, smooth and satiny on inside. Color: Flower throat (inside): 82C. Flower throat vein color (inside): 83A. Flower tube color (outside): 82C. Flower tube vein color (outside): 83A. Petal color, inside: 82C. Petal vein color, inside: 83A. Petal color, outside: 82C. Petal vein color, outside: 83A.

*Sepals.*—Quantity: Five. Size: Length: About 2.2 cm. Width: About 4.7 mm. Shape: Elliptic. Apex: Acute. Margin: Entire. Texture: Pubescent. Aspect: Upright to outward. Color: Inside: 137A. Outside: 144A.

*Pedicel.*—Aspect: Upright. Size: Length: About 2.8 cm. Width: About 1.7 mm. Texture: Pubescent. Color: 144A.

*Reproductive organs.*—Stigma above anthers, superior ovary. Stamens: Stamen number: Five, four are didymous. Anther color: Violet. Filament color: Green white. Pistils: Stigma color: Green. Style color: Yellow green.

Disease resistance: No known Petunia diseases observed to date.

Fruit and seed production: Rarely observed.

*Fruit.*—Capsule with two undivided valves.

*Seeds.*—Minute, spherical.

CHART A

| CHARACTERISTIC | 'SUNVALE' | 'PINK VICTORY' |
|---|---|---|
| PLANT HEIGHT | 19.4 cm | 13 cm |
| PLANT WIIDTH | 52.6 cm | 72.6 cm |
| LEAF SHAPE | Elliptic | Ovate |
| LEAF LENGTH | 5.2 cm | 7.4 cm |
| LEAF WIDTH | 3.2 cm | 43 cm |
| LEAF PUBESCENCE | Moderate | Sparse |
| INTERNODE LENGTH | 2.7 cm | 3.4 cm |
| COROLLA DIAMETER | 7.1 cm | 6 cm |
| TUBE WIDTH | 1.1 cm | 1.7 cm |
| SEPAL WIDTH | 4.7 mm | 63 mm |
| SEPAL SHAPE | Elliptic | Spatulate |
| PEDICEL LENGTH | 2.8 cm | 1.7 cm |
| FLOWER THROAT COLOR | 82C | 85B/85C |
| FLOWER THROAT VEIN COLOR | Purple | Red purple |
| FLOWER TUBE COLOR | 82C | 85B/85C |
| FLOWER TUBE VEIN COLOR | Purple | Yellow green |
| PETAL COLOR, INSIDE | 82C | 82D |
| PETAL VEIN COLOR, INSIDE | Purple | Red purple |
| PETAL COLOR, OUTSDDE | 82C | 76D |
| PETAL VEIN COLOR, OUTSIDE | Purple | Red purple |
| PETAL LOBATION | Shallow | Medium |
| STIGMA RELATIVE TO ANTHERS | Above | Below |
| ANTHER COLOR | Violet | Pale blue |

It is claimed:

1. A new and distinct cultivar of Petunia plant named 'Sunvale', as illustrated and described.

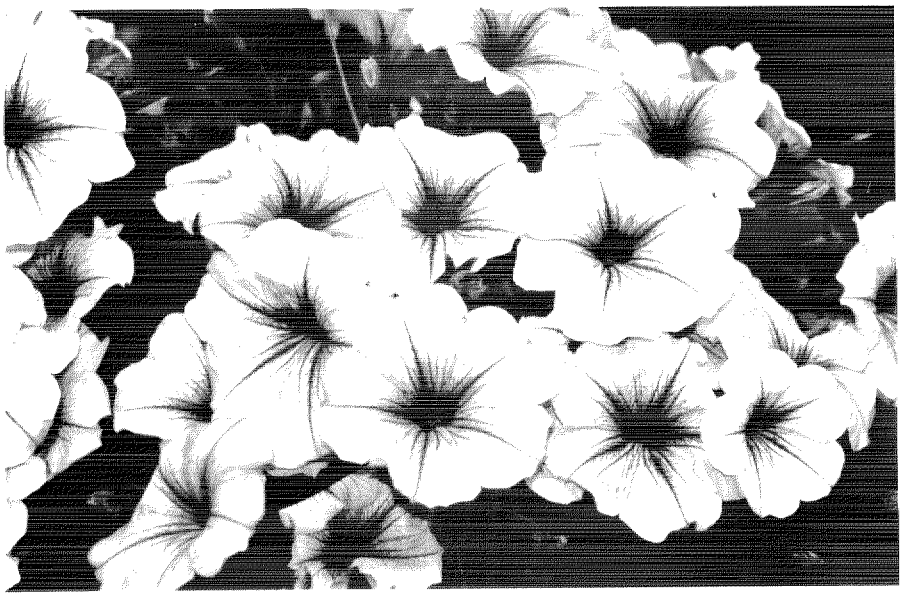

* * * * *